(12) United States Patent
Shang et al.

(10) Patent No.: US 8,209,799 B2
(45) Date of Patent: Jul. 3, 2012

(54) GAP PROTECTION DEVICE FOR EXAMINING TABLE

(75) Inventors: Hong Shang, Shanghai (CN); Ning Tao Yang, Shanghai (CN); Xiang Zhang, Shanghai (CN); Ping Zhu, Shanghai (CN)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/953,156

(22) Filed: Nov. 23, 2010

(65) Prior Publication Data

US 2011/0119830 A1 May 26, 2011

(30) Foreign Application Priority Data

Nov. 26, 2009 (CN) ...................... 2009 2 0271079 U

(51) Int. Cl.
*A47B 7/00* (2006.01)
*A47B 71/00* (2006.01)
*A47C 27/08* (2006.01)
*A47C 31/00* (2006.01)
*B66D 1/36* (2006.01)

(52) U.S. Cl. ............... 5/611; 5/600; 5/424; 5/663; 5/11; 254/280; 254/283; 254/286

(58) Field of Classification Search .............. 5/601, 600, 5/611, 424, 425, 11, 663, 100; 254/280, 254/283, 286
See application file for complete search history.

(56) References Cited

U.S. PATENT DOCUMENTS

| 5,084,925 A | 2/1992 | Cook |
| 5,943,714 A * | 8/1999 | Dignam ........................... 5/10.1 |
| 5,987,666 A | 11/1999 | Zigmont |
| 2005/0125899 A1* | 6/2005 | Hanson et al. ..................... 5/613 |
| 2007/0226901 A1* | 10/2007 | Pervorse et al. ................... 5/118 |

* cited by examiner

*Primary Examiner* — Jonathan Liu
(74) *Attorney, Agent, or Firm* — Lempia Summerfield Katz LLC

(57) ABSTRACT

A gap protection device for an examining table includes a guide rail, a protecting chain and a rigid rope. The guide rail is fixed onto the non-moving part of the examining table. One end of the protecting chain is fixed onto the body of the examining table and is movable along the guide rail so as to cover the gap between the body and the non-moving part of the examining table. The two ends of the rigid rope are respectively connected to the two ends of the protecting chain. When the examining table is moved, the closed loop formed by the protecting chain and the rigid rope circulates synchronously under the drive of the examining table, such that the protecting chain covers the gap between the body and the non-moving part of the examining table.

7 Claims, 4 Drawing Sheets

Prior Art

GAP PROTECTION DEVICE FOR EXAMINING TABLE

This application claims the benefit of CN 200920271079.6, filed Nov. 26, 2009.

BACKGROUND

The present embodiments relate to a gap protection device for an examining table.

A conventional medical examining table, such as an MRI examining table, has two functions: horizontal movement and vertical movement, so as to carry a patient vertically or horizontally according to the requirements for diagnosis. The gap between the body and the non-moving part of the examining table may not be covered with a fixed cover shell. Otherwise, the cover shell may collide with the table body when the table body is moving, which inconveniences the medical diagnosis.

As shown in FIG. 1, in order to provide smooth movement of the examining table, a gap 10 may be reserved between the table body and the non-moving part of the examining table. However, if the finger of a patient enters the gap 10 accidentally when the examining table is moving, the finger may be hurt or even broken.

SUMMARY AND DESCRIPTION

The present embodiments may obviate one or more of the drawbacks or limitations in the related art. For example, a gap protection device for an examining table that may cover the gap between a body and a non-moving part of the examining table may be provided. A gap protection device for an examining table that is not affected by the magnetic field working environment of the examining table may also be provided.

A gap protection device for an examining table includes a guide rail, a protecting chain, a rigid rope and a roller. The guide rail may be fixed onto the non-moving part of the examining table. One end of the protecting chain is connected to the body of the examining table and is slidable along the guide rail to cover the gap between the body and the non-moving part of the examining table. The two ends of the rigid rope are respectively connected to the two ends of the protecting chain, making the rope and the chain form a closed loop. The roller is fixed onto the non-moving part of the examining table, with the rigid rope being wound around the roller.

In one embodiment, the gap protection device includes a guide part. The guide part is connected to the one end of the protection chain connected to the examining table, and the rigid rope is wound around the guide part.

In another embodiment, the gap protection device includes a mounting plate. The mounting plate is fixed on the body of the examining table. The guide part is fixed on the mounting plate, and the rigid rope is wound around the guide part and is fixed on the mounting plate.

In yet another embodiment, the gap protection device includes a set of springs, with one end of each of the springs being connected to a rolling shaft of the roller, and the other end of each of the springs being fixed on the non-moving part of the examining table.

In one embodiment of the gap protection device, the protection chain is a plastic chain, and the plastic chain is formed by a plurality of plastic chain plates that are connected in succession. In another embodiment, the rigid rope is a steel wire rope.

By way of the full-circulation structure of the protecting chain and the rigid rope of the gap protection device of the present embodiments, the gap between the table body and the non-moving part of the examining table may be effectively protected, thus ensuring safety in operation. The arrangement of the roller and the spring may provide a buffer to the gap protection device and make the movement of the device more stable.

The gap protection device of the present embodiments is subject to an evenly applied force, has good durability, simple structure and low costs for manufacturing. The main parts of the gap protection device are made of non-magnetic materials so the main parts do not tend to have any influence on the magnetic environment.

DETAILED DESCRIPTION OF THE DRAWINGS

Embodiments of the present invention are described here with reference to the accompanying drawings. In each of the figures, parts with the same or similar functions are represented with the same numerals.

Figure 1:
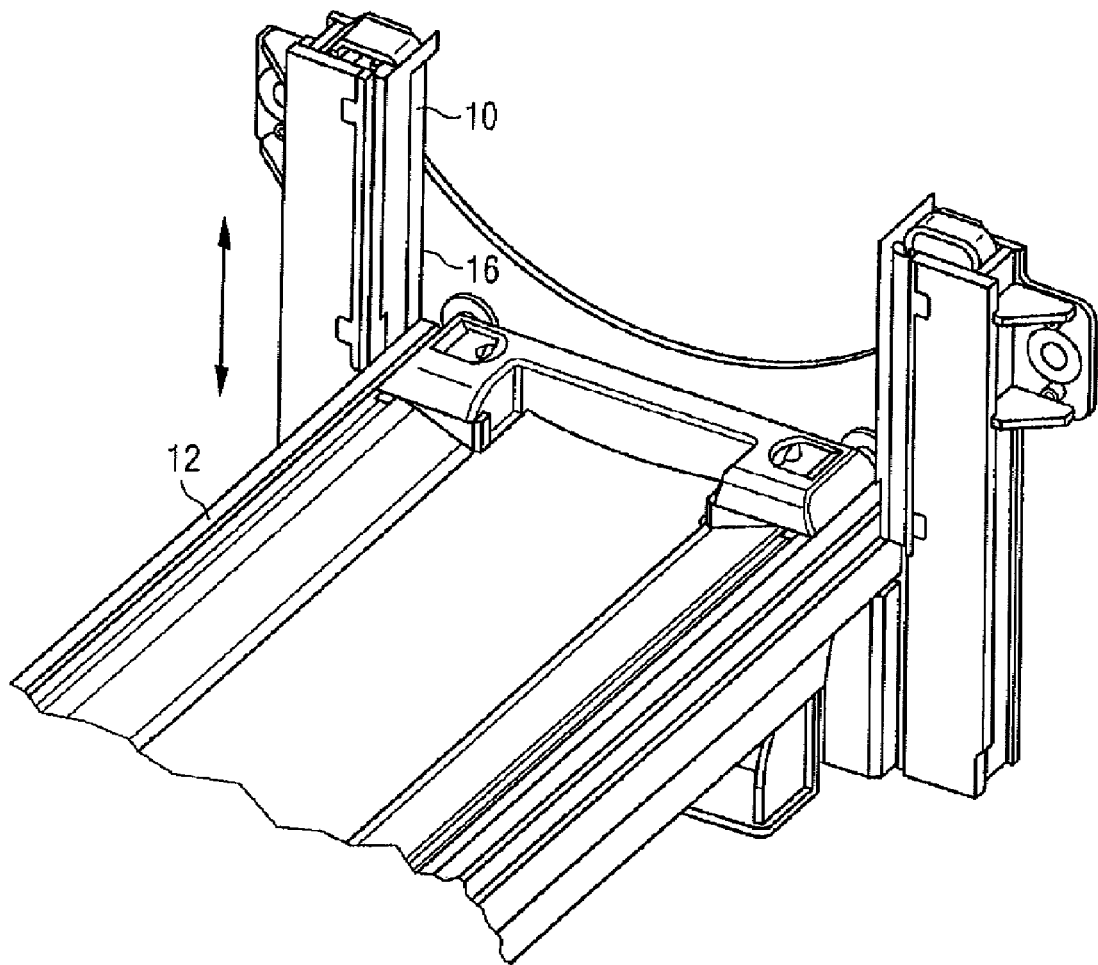
FIG. 1 is a schematic diagram of an examining table.
Figure 2:
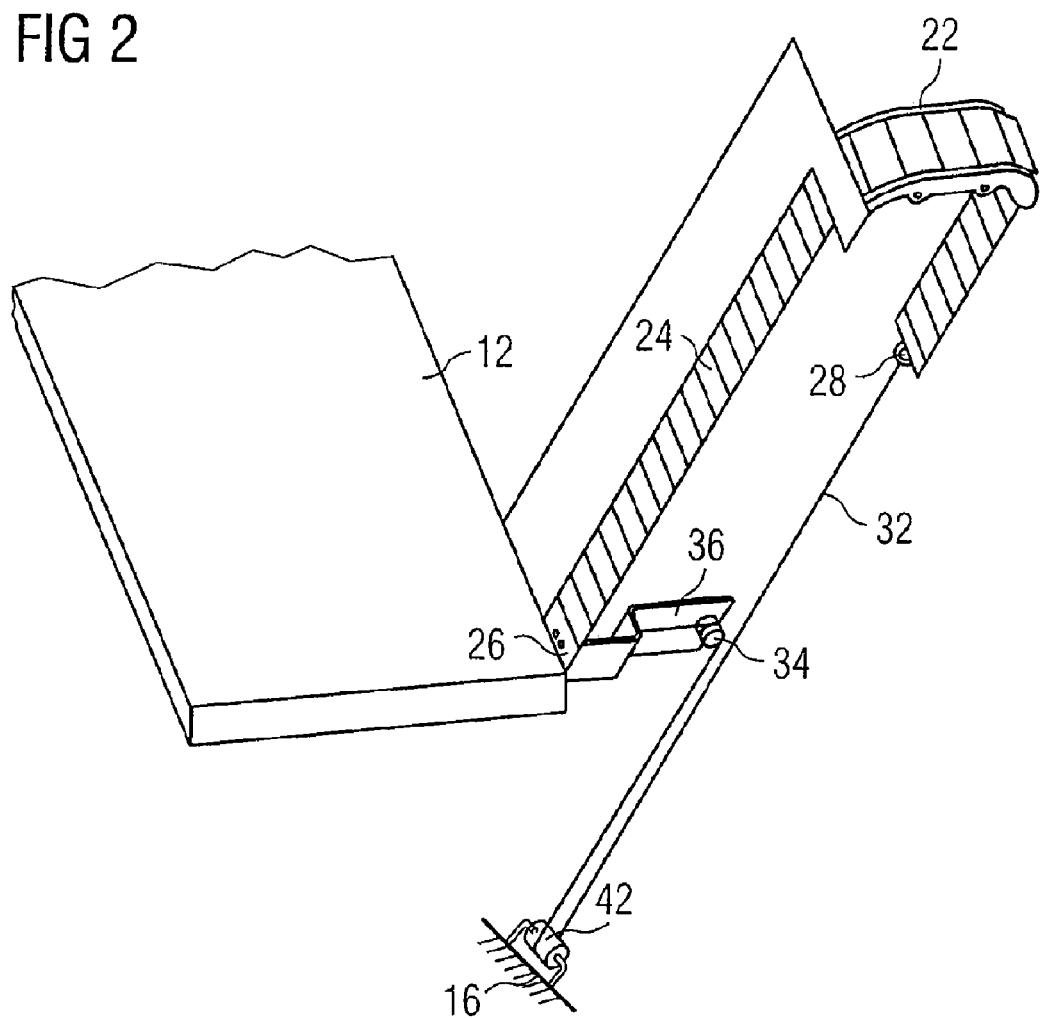
FIG. 2 is a schematic diagram of one embodiment of a gap protection device for an examining table.
Figure 4:
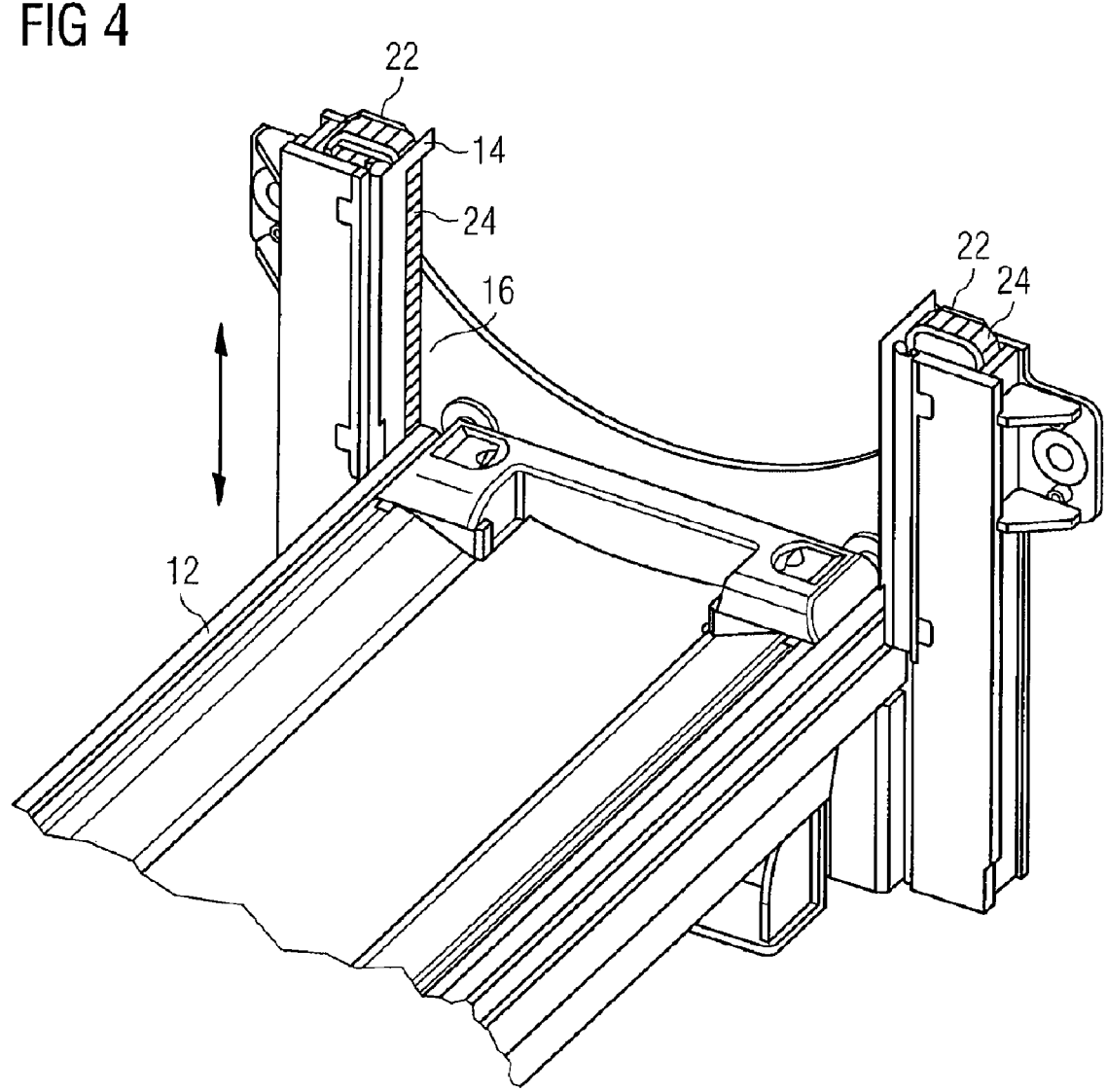
FIG. 4 is a schematic diagram of one embodiment of the gap protection device shown in FIG. 3 in an operating state.

A gap protection device for an examining table, as shown in FIG. 2, includes a guide rail 22, a protecting chain 24, a rigid rope 32 and a roller 42. The guide rail 22 and the roller 42 are fixed onto a non-moving part 16 of the examining table (as shown in FIG. 4). "Non-moving part" may not refer to any singular part of the examining table, but may refer generally to the fixed parts of the examining table. The Examining table is for an MRI or a CT system.

A first end 26 of the protecting chain 24 is connected to the table body 12. The protecting chain 24 may slide along the guide rail 22 to cover a gap between the table body 12 and the non-moving part 16 of the examining table. When the table body 12 is moved along a vertical direction (e.g., the direction indicated by the arrow in FIG. 4), the protecting chain 24 moves synchronously to cover the gap between the table body 12 and the non-moving part 16 of the examining table with the protecting chain 24.

As shown in FIG. 2, the gap protection device of the present embodiments may include a guide part 34. The guide part 34 is connected to the first end 26 of the protecting chain 24 connected to the table body 12. The rigid rope 32 is wound around the guide part 34. The guide part 34 may be either a rotatable guide pulley or a fixed guide structure, for example.

In one embodiment, the protecting chain 24 is made of a non-magnetic material such as, for example, plastic. The plastic chain may be formed by a plurality of plastic chain plates joined in succession and disposed on the guide rail 22. The plurality of plastic chain plates may be slidable back and forth along the guide rail 22. Free rotation between any two of the plastic chain plates on the plastic chain is prevented, so the plastic chain may bend in one direction to wind around the guide rail while not bending in the opposite direction, thus avoiding hurting the fingers of a patient.

As shown in FIG. 2, one end of the rigid rope 32 is fixed onto a second end 28 of the protecting chain 24, and another end of the rigid rope 32 is fixed onto the first end 26 of the protecting chain 24, the rigid rope 32 winding around the guide part 34 and the roller 42, thus forming a closed loop.

The rigid rope 32 may be any number of materials such as, for example, a steel wire rope or a nylon rope. The roller 42 is fixed onto the non-moving part 16 of the examining table. Therefore, the table body may move synchronously with the protecting chain 24 and the rigid rope 32.

As shown in FIG. 2, in one embodiment, the gap protection device includes a mounting plate 36. The mounting plate 36 may be fixed onto the body 12 of the examining table, and the guide part 34 is fixed onto the mounting plate 36 to connect the protecting chain 24 via the mounting plate 36. The rigid rope 32 is fixed onto the mounting plate 36 and winds around the guide part 34 to achieve the connection to the protecting chain 24. The embodiment shown in FIG. 2 makes the connection between the protecting chain 24, the table body 12 and the rigid rope 32 more stable, and at the same time, the wiring of the rigid rope 32 more compact and regular (e.g., to realize the design of a rigid rope circulating structure in a tight space).

Figure 3:
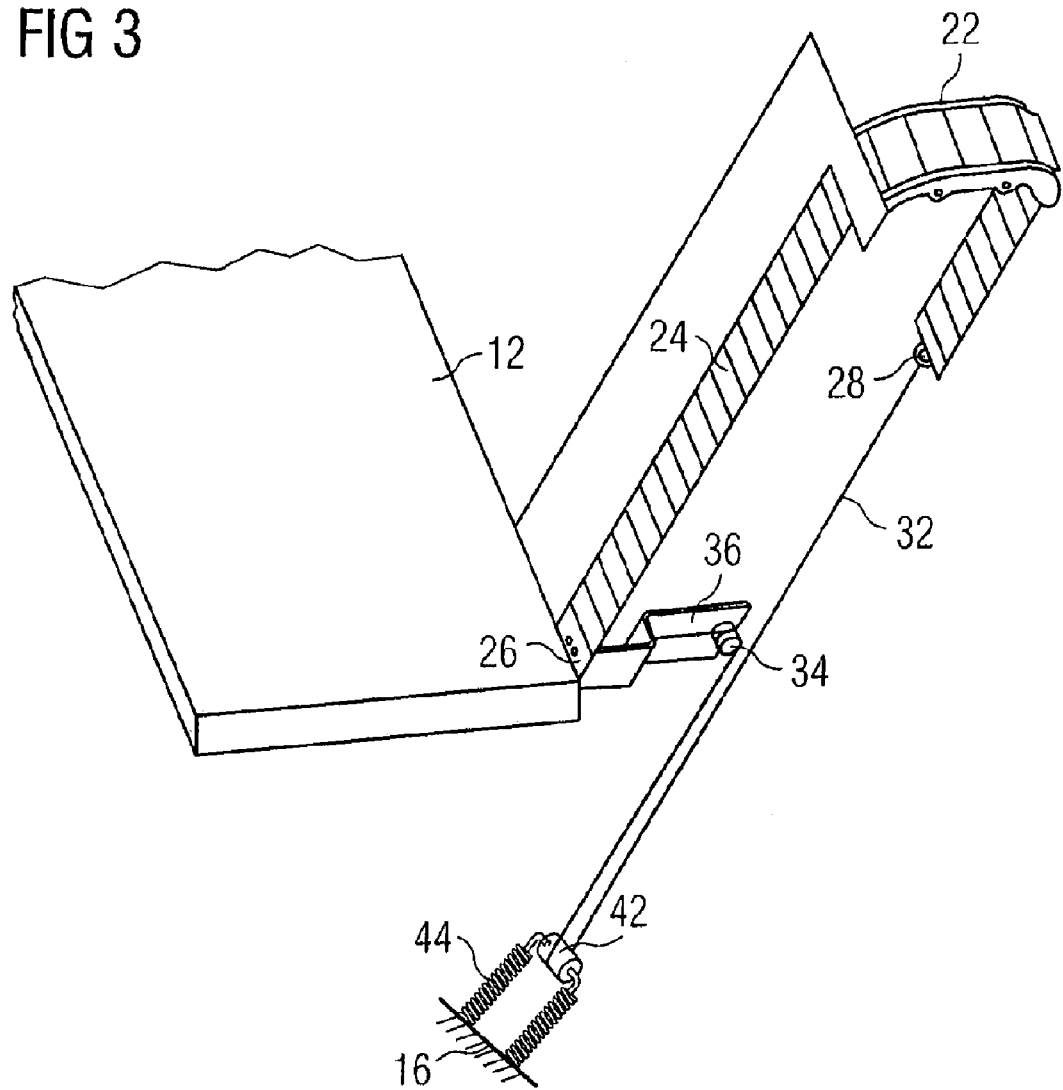
FIG. 3 is a schematic diagram of another embodiment of the gap protection device for an examining table.

As shown in FIG. 3, in order to further increase the stability of the gap protection device, the gap protection device may include a set of springs 44. One end of each spring 44 is connected to the roller 42, and another end of each spring 44 is fixed onto the non-moving part 16 of the examining table. The springs 44 are for pre-tensioning and for providing a proper buffer for the gap protection device to increase stability of the gap protection device. The springs 44 may not extend or compress significantly along with the movement of the rigid rope 32. The springs 44 are disposed at a position far away from the operating magnetic field, so the springs 44 may not be affected by the magnetic field.

The operation process of the gap protection device of the present embodiments is described below in conjunction with FIG. 4. As shown in FIG. 4, the gap protection device of the present embodiments is disposed on each of two sides of the examining table body 12. The protecting chain 24 covers a gap beside a cover shell 14 for protection, thus preventing any foreign matter from entering the gap accidentally when the examining table is moving. According to various diagnosis requirements, when the table body 12 is moving vertically up along the direction indicated by the arrow in FIG. 4, the closed loop formed by the protecting chain 24 and the rigid rope 32 (e.g., show in FIG. 2 or 3) circulates synchronously under the drive of the table body 12, thus completely covering the gap beside the cover shell 14 as the protecting chain 24 slides around the guide rail 22. When the table body 12 moves vertically down along the direction indicated by the arrow in FIG. 4, the closed loop formed by the protecting chain 24 and the rigid rope 32 circulates synchronously in the opposite direction, thus completely covering the gap beside the cover shell 14 in the same way.

Although the operating procedure of the gap protection device is described above in conjunction with the vertical movement of the examining table, the gap protection device may also be used in a horizontal movement structure for the examining table and may also serve to prevent foreign matter from entering the gap between the table body and the non-moving part.

Since the protecting chain and the rigid rope form a closed loop in the gap protection device of the present embodiments, such a full-circulation movement makes the structure more stable and the force applied more uniform. In one embodiment, the possibility that the transmission part is magnetized and thus affects the operation magnetic field may be avoided since the protecting chain is made of, for example, plastic. The plastic chain of the present embodiments is formed by a plurality of plastic chain plates joined in succession, which significantly reduces the flexibility and thus increases the stability and durability of the plastic chain.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A gap protection device for an examining table including a non-moving part and a body, the gap protection device comprising:
    a guide rail fixed onto the non-moving part of the examining table;
    a protecting chain comprising a first end and a second end, the first end of the protecting chain being connected to the body of the examining table and being slidable along the guide rail, so as to cover a gap between the body and the non-moving part of the examining table;
    a rigid rope comprising a first end and a second end, the first and second ends of the rigid rope being respectively connected to the first and second ends of the protecting chain; and
    a roller fixed onto the non-moving part of the examining table,
    wherein the rigid rope is wound around the roller.

2. The gap protection device as claimed in claim 1, further comprising a guide part, the guide part being connected to the first end of the protecting chain,
    wherein the rigid rope is wound around the guide part.

3. The gap protection device as claimed in claim 2, further comprising a mounting plate, the mounting plate being fixed onto the body of the examining table,
    wherein the guide part is fixed onto the mounting plate, and
    wherein the rigid rope is wound around the guide part and fixed on the mounting plate.

4. The gap protection device as claimed in claim 1, further comprising a set of springs, a first end of each of the springs being connected to a rolling shaft of the roller, and a second end of each of the springs being fixed on the non-moving part of the examining table.

5. The gap protection device as claimed in claim 1, wherein the protecting chain is a plastic chain, and
    wherein the plastic chain comprises a plurality of plastic chain plates that are connected in succession.

6. The gap protection device as claimed in claim 1, wherein the rigid rope is a steel wire rope.

7. The gap protection device as claimed in claim 1, wherein the roller is fixed onto the non-moving part of the examining table, such that the body of the examining table moves synchronously with the protecting chain and the rigid rope.

* * * * *